(12) United States Patent
Michelson

(10) Patent No.: US 7,244,275 B2
(45) Date of Patent: Jul. 17, 2007

(54) ORTHOPEDIC IMPLANT SURFACE CONFIGURATION WITH A PROJECTION HAVING A BACK CUT

(75) Inventor: Gary K. Michelson, Venice, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 507 days.

(21) Appl. No.: 10/697,835

(22) Filed: Oct. 30, 2003

(65) Prior Publication Data

US 2005/0021150 A1    Jan. 27, 2005

Related U.S. Application Data

(60) Division of application No. 09/572,518, filed on May 17, 2000, now Pat. No. 7,115,143, which is a continuation-in-part of application No. 09/457,228, filed on Dec. 8, 1999, now Pat. No. 6,827,740.

(51) Int. Cl.
*A61F 2/28* (2006.01)
*A61F 2/36* (2006.01)
*A61F 2/44* (2006.01)

(52) U.S. Cl. ............... 623/23.5; 623/16.11; 623/17.11; 623/20.14

(58) Field of Classification Search ............. 623/16.11, 623/171, 17.15, 18.11, 20.14, 20.5, 22.32, 623/23.26, 23.29, 23.31, 20.7, 22.36; 606/61, 606/68–72

See application file for complete search history.

(56) References Cited

U.S. PATENT DOCUMENTS

| 4,349,921 A | 9/1982 | Kuntz |
| 4,531,244 A | 7/1985 | Hamas |
| 4,673,409 A | 6/1987 | Van Kampen |

(Continued)

FOREIGN PATENT DOCUMENTS

EP    0 637 440    2/1995

(Continued)

OTHER PUBLICATIONS

U.S. Appl. No. 09/921,844, filed Aug. 3, 2001, Michelson.

*Primary Examiner*—David J. Isabella
(74) *Attorney, Agent, or Firm*—Martin & Ferraro, LLP

(57) ABSTRACT

The present invention is a specialized orthopedic implant having an exterior surface for engaging bone. The surface comprises arrayed projections having at least one forward facing facet directed at least in part toward the leading end of the implant and at least one rearward portion directed at least in part toward the opposite trailing end of the implant. Each of the forward facet and rearward portion has a length and a slope. The length of the forward facet is longer than the length of the rearward facet. The slope of the rearward facet is steeper than the slope of the forward facet. The surface projections also have opposed side facets directed generally toward the sides of the implant. The side facets are located between the forward facet and rearward facet and converge toward each other in a direction away from the base of the surface projections. The surface may also include projections having left and right forward side facets and a rearward facet. The surface further may include projections having left and right rearward side facets and a forward facet.

226 Claims, 8 Drawing Sheets

U.S. PATENT DOCUMENTS

| | | |
|---|---|---|
| 4,795,472 A | 1/1989 | Crowninshield et al. |
| 4,834,757 A | 5/1989 | Brantigan |
| 4,865,603 A | 9/1989 | Noiles |
| 4,944,763 A | 7/1990 | Willert et al. |
| 4,955,907 A | 9/1990 | Ledergerber |
| 5,019,107 A | 5/1991 | Schelhas |
| 5,258,031 A | 11/1993 | Salib et al. |
| 5,306,308 A | 4/1994 | Gross et al. |
| 5,425,772 A | 6/1995 | Brantigan |
| 5,522,899 A | 6/1996 | Michelson |
| 5,553,476 A | 9/1996 | Oehy et al. |
| 5,593,409 A | 1/1997 | Michelson |
| 5,609,635 A | 3/1997 | Michelson |
| 5,683,464 A | 11/1997 | Wagner et al. |
| 5,713,899 A | 2/1998 | Marnay et al. |
| 5,716,412 A | 2/1998 | DeCarlo, Jr. et al. |
| 5,755,799 A | 5/1998 | Oehy et al. |
| 5,860,973 A | 1/1999 | Michelson |
| 5,865,845 A | 2/1999 | Thalgott |
| 5,888,227 A | 3/1999 | Cottle |
| 5,899,941 A | 5/1999 | Nishijima et al. |
| 5,989,289 A | 11/1999 | Coates et al. |
| 6,019,793 A | 2/2000 | Perren et al. |
| 6,080,158 A | 6/2000 | Lin |
| 6,087,555 A | 7/2000 | Dunstan et al. |
| 6,143,033 A | 11/2000 | Paul et al. |
| 6,174,334 B1 | 1/2001 | Suddaby |
| 6,190,414 B1 | 2/2001 | Young et al. |
| 6,258,125 B1 | 7/2001 | Paul et al. |
| 6,325,827 B1 | 12/2001 | Lin |
| 6,425,920 B1 | 7/2002 | Hamada |
| 6,432,106 B1 | 8/2002 | Fraser |
| 6,482,233 B1 | 11/2002 | Aebi et al. |
| 6,511,509 B1 | 1/2003 | Ford et al. |
| 6,592,624 B1 | 7/2003 | Fraser et al. |
| 6,660,038 B2 | 12/2003 | Boyer, II et al. |
| 2002/0068978 A1 | 6/2002 | Camino et al. |

FOREIGN PATENT DOCUMENTS

| | | |
|---|---|---|
| SU | 1 107 854 | 8/1984 |
| WO | WO 98/58604 | 12/1998 |

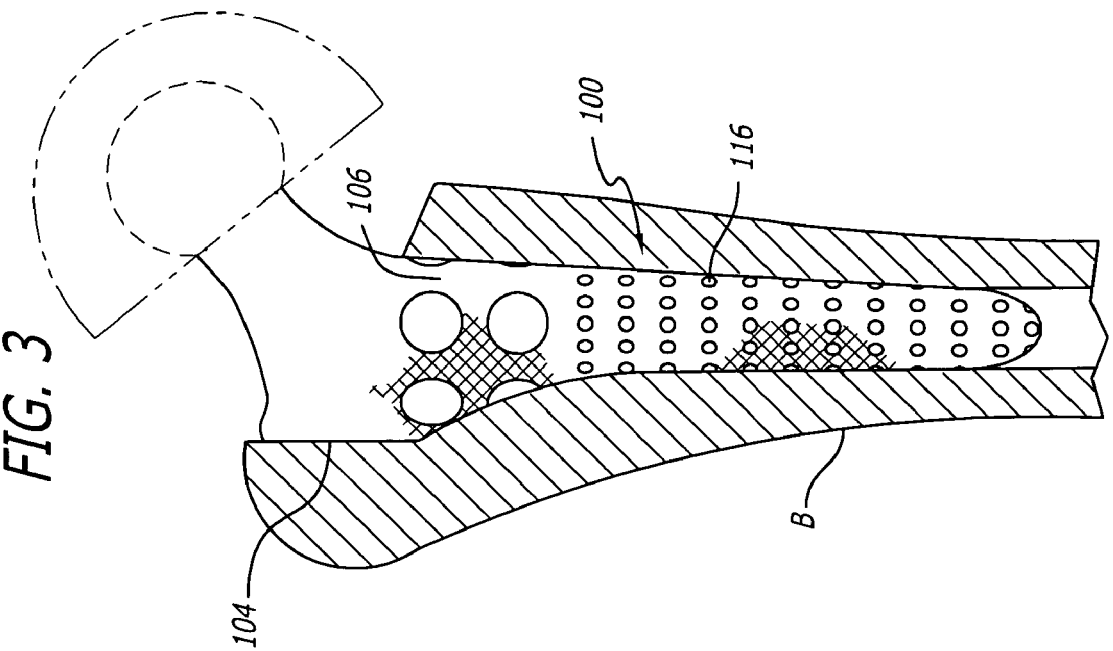
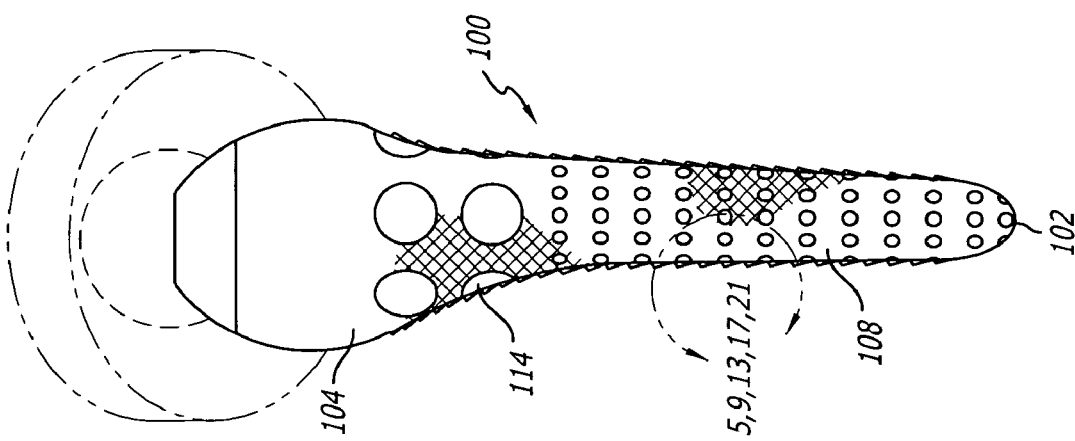
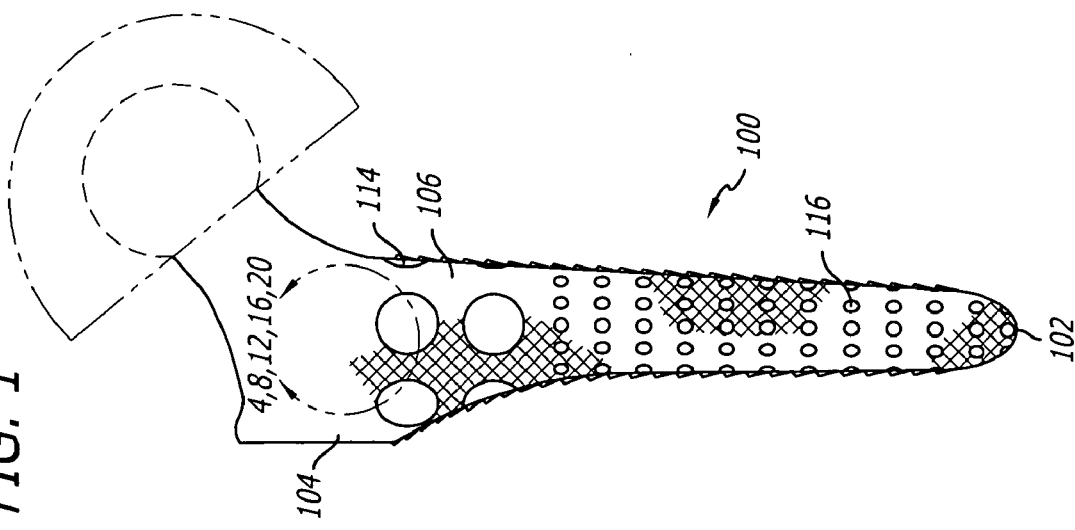

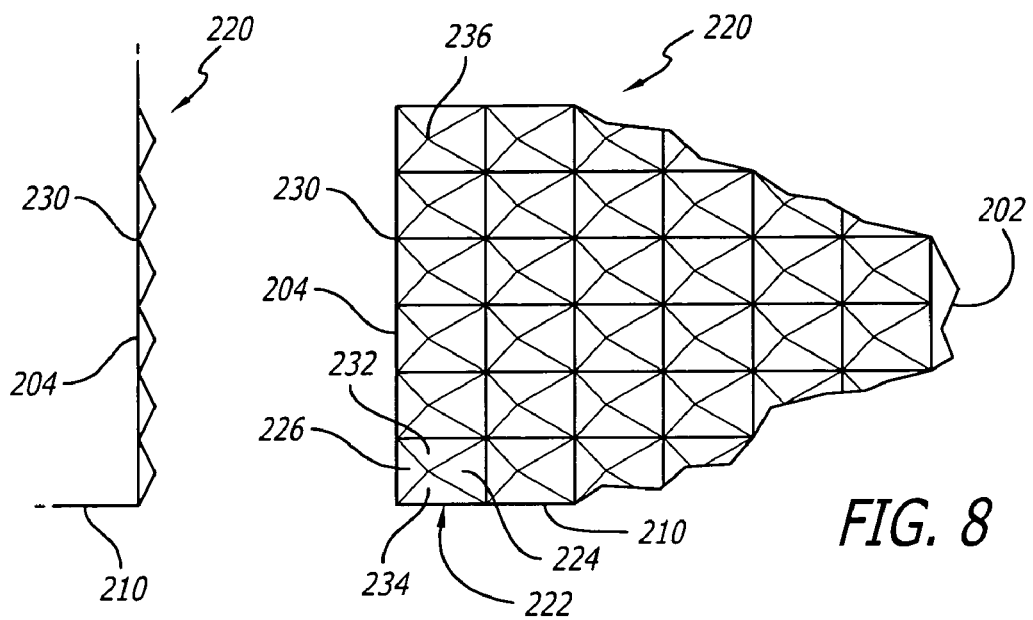
FIG. 10
FIG. 8
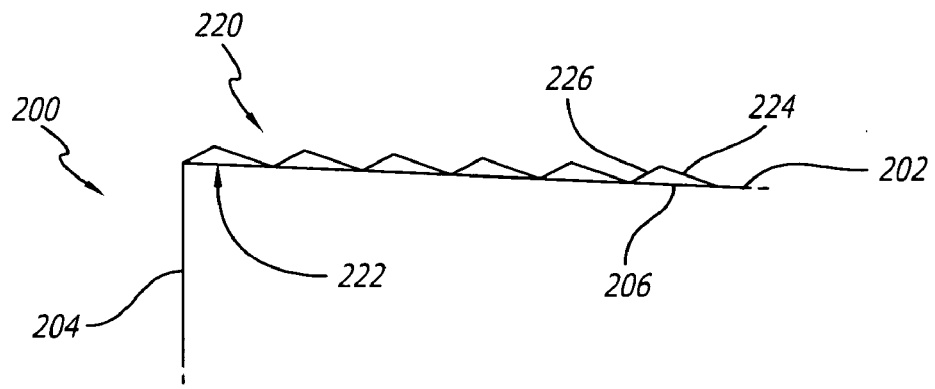
FIG. 9
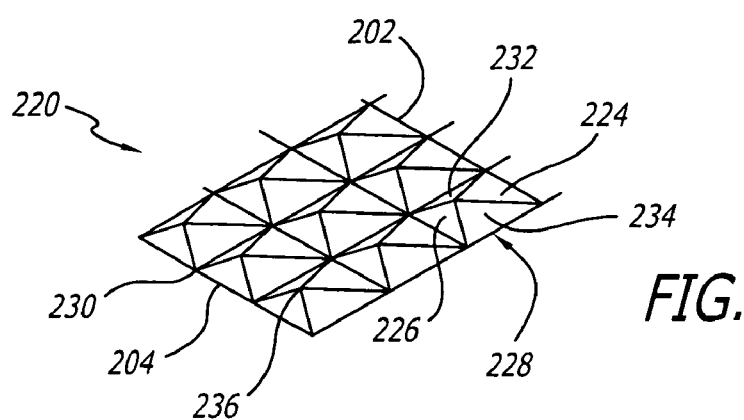
FIG. 11

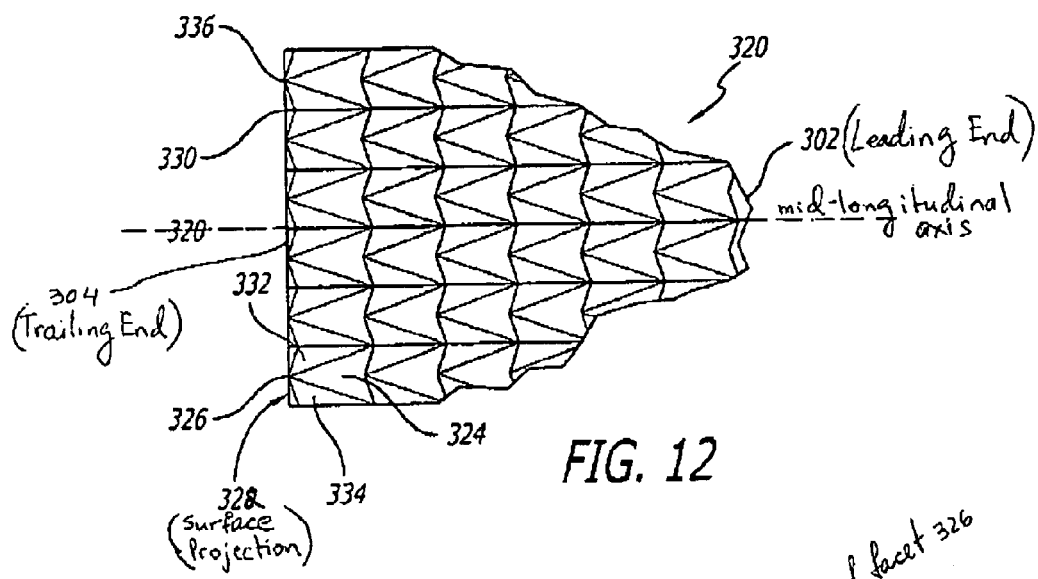
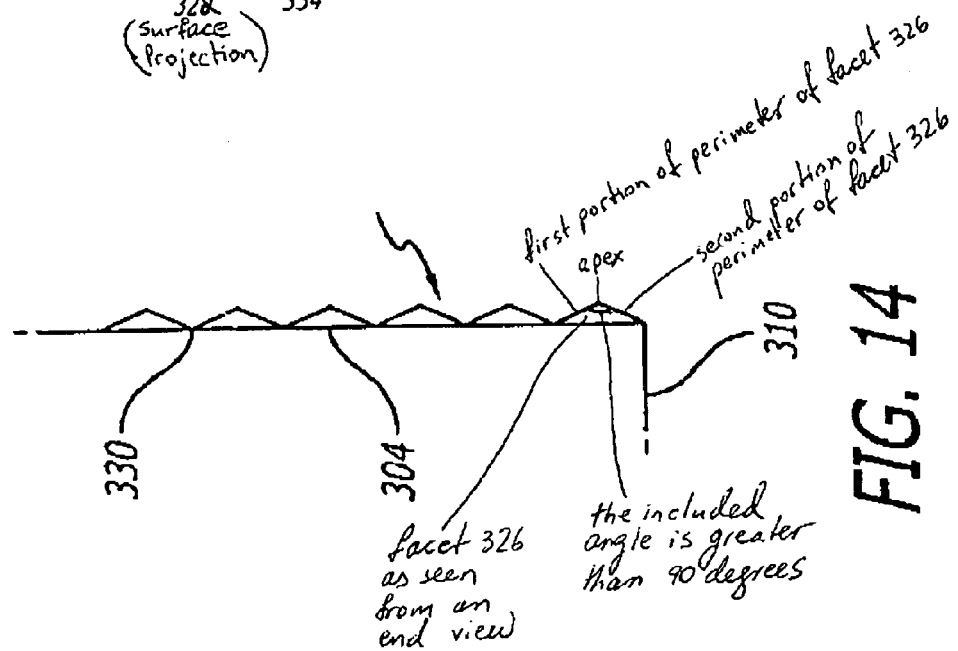

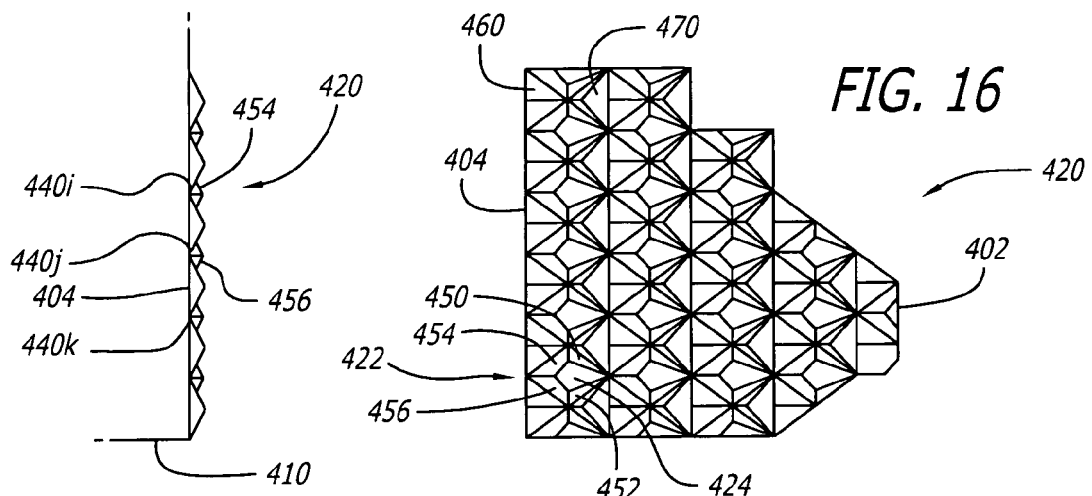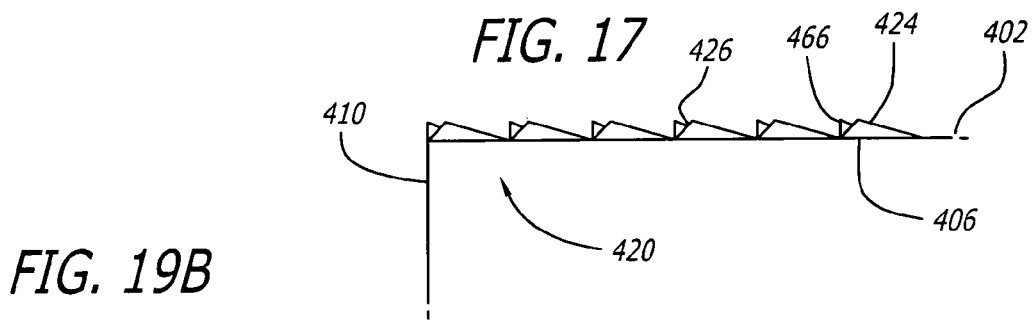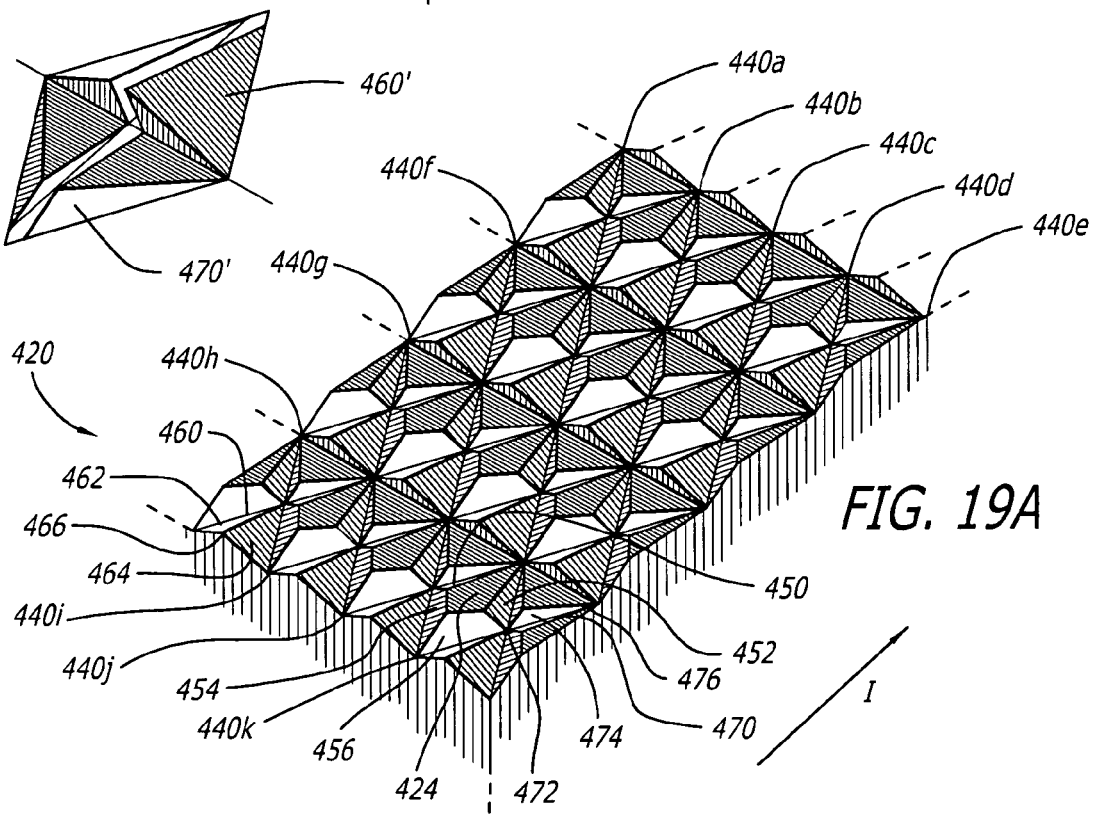

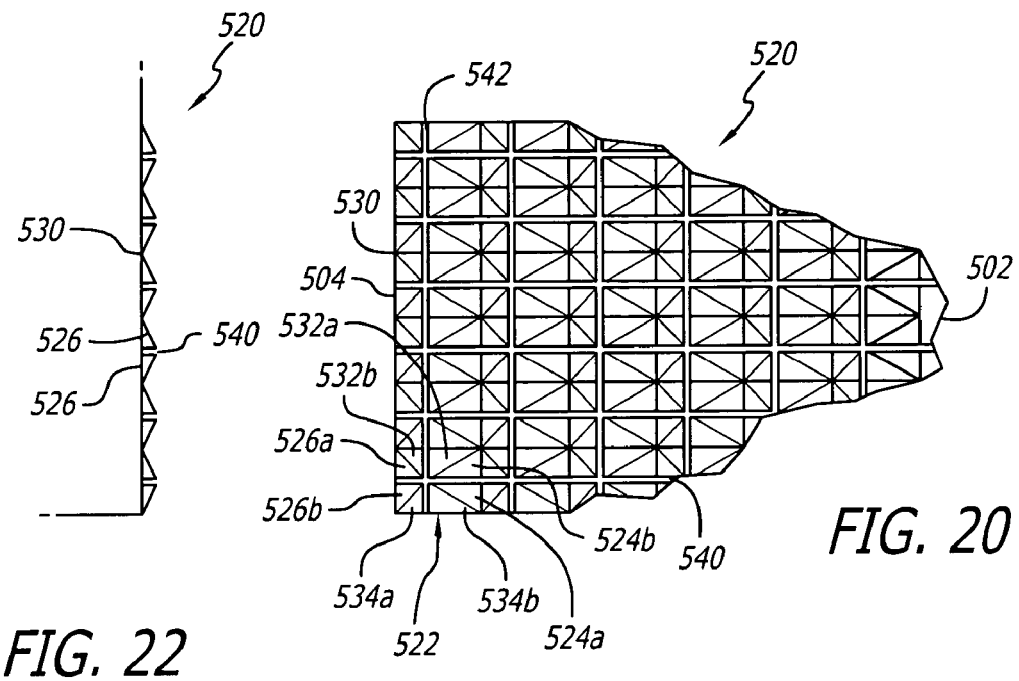
FIG. 22
FIG. 20
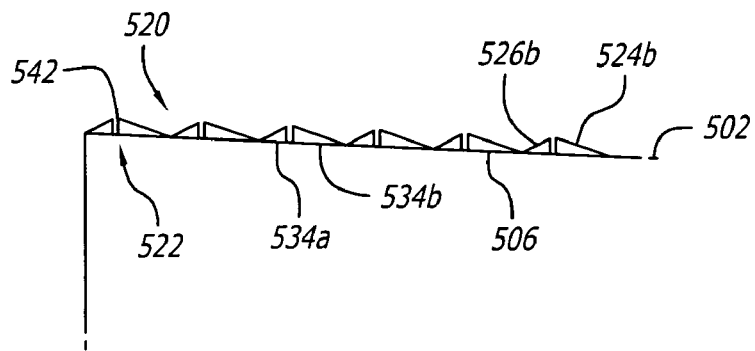
FIG. 21
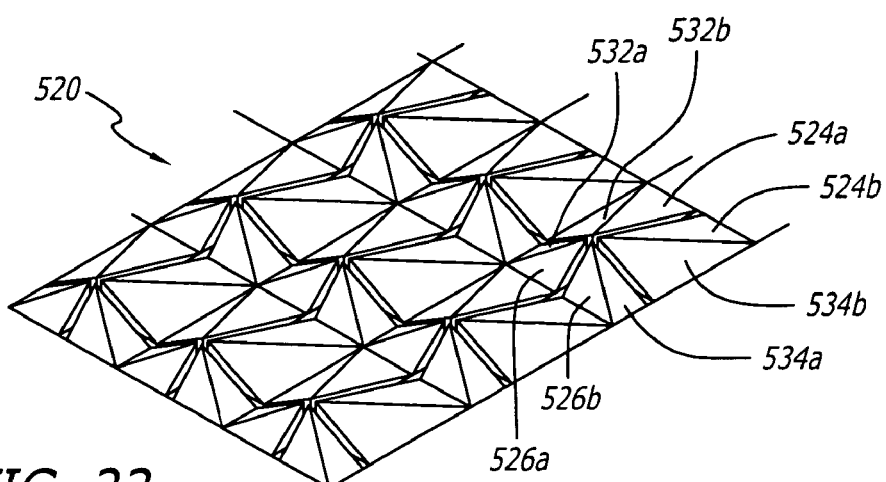
FIG. 23

ORTHOPEDIC IMPLANT SURFACE CONFIGURATION WITH A PROJECTION HAVING A BACK CUT

RELATED APPLICATION

This application is a divisional of application Ser. No. 09/572,518, filed May 17, 2000 now U.S. Pat. No. 7,115,143; which is a continuation-in-part of application Ser. No. 09/457,228, filed Dec. 8, 1999 now U.S. Pat. No. 6,287,740; all of which are incorporated herein by reference.

BACKGROUND OF THE INVENTION

Description of the Related Art

The present invention relates to orthopedic implants for placement at least in part into bone, or for placement at least in part between adjacent bones or bone portions of a human skeleton. The orthopedic implants of the present invention have a specialized surface for engaging bone.

Vital to the functioning of such orthopedic implants is their ability to remain properly located within bone after installation. In U.S. Pat. Nos. 5,593,409 and 5,609,635, Michelson described the use of surface roughenings, such as knurling or ratcheting on the opposed upper and lower vertebral body engaging surfaces of interbody spinal fusion implants. Knurling has been particularly beneficial for increasing the grip of the implant surface to the bone of the adjacent vertebral bodies in a rather uniform manner without a directional bias. Orthopedic implants inserted at least in part into bone, have a propensity to move in a particular direction, which is opposite to their path of insertion, because this is the path of least resistance. Such propensity to move is further increased when the implant has an overall configuration that is tapered along at least a portion of its length such that the bone engaging surfaces of the implant are in angular relationship to each otherand are spaced further apart at the implant's trailing end than at the implant's leading end. In such circumstances where it is desirable then to gain stability in resistance to a particular direction of movement of the orthopedic implant, the use of a plurality of forward facing ratchetings on the implant's bone engaging surfaces has been preferable to the previously described knurling for that purpose.

The term "ratcheting" as used herein is defined as a plurality of angular teeth or ridges or protrusions projecting from the surface of an implant to resist motion of the implant at least in one direction. The phrase "forward facing ratchetings" as used herein is defined as a ratcheting having at least one forward facing facet having a length greater than a rearward facing facet and an angle from the implant surface from which the forward facing facet arises that is less steep than the angle of the rearward facet. On an implant surface, forward facing ratchetings facilitate the insertion of the implant in one direction and after insertion, resisting movement of the implant in a direction opposite to the direction of insertion. An example of forward facing ratchetings of the prior art is shown in partial fragmentary view in FIGS. 24A and 24B, generally referred to by the reference numeral 50.

Knurled surfaces of the related art provide some stability in all directions, but lack the ability to resist a particular direction of motion preferentially. The above-described ratcheted surface best resists motion in a particular direction. There exists a need for an improved orthopedic implant surface configuration, wherein the bone engaging surfaces of the implant are configured to be resistant to implant movement in all directions, and preferentially in particularly one direction.

SUMMARY OF THE INVENTION

The present invention relates to orthopedic implants having a specialized surface configuration on at least a portion of the exterior surfaces adapted for engaging bone, including adjacent bones and bone portions, into which the implant is to be implanted. Such an implant surface configuration has utility with a wide variety of shapes of orthopedic implants where enhanced skeletal fixation is desired. Such an implant surface configuration can provide for enhanced stability, increased surface area, and a surface for the delivery of fusion promoting substances other than bone. In a preferred embodiment, the implant surface can provide for resisting motion in all directions, and particularly in at least one direction, such as counter to the direction of insertion of the implant.

While various embodiments of the present invention are presented by way of example only and not limitation, common to each of them is that the surface configuration incorporates a plurality of spatially integrated surface projections having at least one forward facing facet directed at least in part toward the leading end of the implant and at least one rearward portion directed at least in part toward the opposite trailing end of the implant. By way of example and not limitation, the rearward portion may be a facet, a line, or an edge of the rearward aspect of the surface projection formed where two facets come together. Each of the forward and rearward facets have a length and a slope. The length of the forward facet is longer than the length of the rearward facet. The slope of the rearward facet is steeper than the slope of the forward facet. In various embodiments, the surface projections also have opposed side facets directed generally toward the sides of the implant. The side facets are located between the forward facet and rearward facet and may converge toward each other in a direction away from the base of the surface projections. The surface comprises multifaceted ratcheted projections that are organized in geometrically disposed fields or arrays which are at a minimum located on at least a portion of the bone engaging surfaces of the implant. From the teachings disclosed herein, it is appreciated that the surface projections can be geometrically arranged in a pattern wherein at least a portion of the projection is aligned along a longitudinal, horizontal, diagonal, or curved line. The bone engaging surfaces of the implant can be at least in part arcuate or planar and can converge along a portion or all of the length of the implant.

In various preferred embodiments of the present invention, the rearward facets of the surface projections can be perpendicular or at angles greater or less than 90 degrees to exterior surface of the implant from which the projections arise. The opposed side facets of the surface projections can have at least a first portion in a plane at an angle to the longitudinal axis of the implant. The opposed side facets can intersect each other, and can converge to form a peak at the top of each of the surface projections. The peaks can be aligned along lines that are perpendicular, parallel, or diagonal to the longitudinal axis of the implant. The surface projections can be cleaved such as by longitudinal and/or horizontal cuts to increase the number of exposed sides of the projections and thus increase the available surface area to contact and engage the bone adjacent the implant and increase the number of recessed areas to contain material such as fusion promoting substances for example. Alternatively, the peaks of each surface projection can be cleaved, truncated, or flattened at least in part.

The surface projections can include a left forward side facet and a right forward side facet directed toward the leading end and sides, respectively, of the implant. Similarly, the surface projections can include a left rearward side facet and a right rearward side facet directed toward the trailing end and sides, respectively, of the implant. The side facets of adjacent surface projections can be spaced apart to define a groove therebetween. A plurality of adjacent surface projections can be spaced apart to form a plurality of grooves that can be parallel or at an angle to the longitudinal axis of the implant, wherein the angle can be less than 90 degrees. The grooves can have a horizontal cross section that is a V-shape, U-shape, or a box-like shape, for example.

Sequential projections can be positioned on an implant wherein each surface projection has forward facing facets facing the same direction, such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface contour suitable for the intended use. The surface projections can be oriented relative to one another to form fields or arrays that further can be geometrically disposed relative to one another, preferably in a pattern wherein at least a portion of the projection is aligned along a longitudinal, horizontal, diagonal, or curved line.

The surface configuration of the present invention can be formed by casting, machining, or any other techniques known to one of ordinary skill in the art. The present surface configuration may readily be machined by milling the implant surface from side to side, across the bone engaging surfaces, to form ratchetings generally disposed perpendicular to the long axis of the implant and generally formed facing to the insertion end of the implant. The ratchetings may be cross machined with an angled cutting face to form grooves passing through the ratchetings. For example, a milling machine having a cutting tool, with a V-shaped profile, can be run through the plurality of ratchetings parallel to the longitudinal axis of the implant to form the above-described surface. In a preferred embodiment, the V-shaped cutting tool of the milling machine has opposed cutting faces with an angle of approximately 90 degrees to each other, which faces are each at a 45-degree angle to the plane of the surfaces being machined. Without departing from the scope of the present invention, the angle of the cutting faces can be more or less than 90 degrees, and the angle of the cutting face to the surface to be cut can be more or less than 45 degrees. It is appreciated that rather than the cutting element being run parallel to the longitudinal axis of the implant, the cutting element could be run at some other angle. By way of example only and not limitation, this angle could be at 45 degrees to the longitudinal axis of the implant and to the projections. Each surface projection could then be formed by a cutter crossing in two passes to form two grooves at a 90 degree angle to each other.

The surface configuration of the implant of the present invention may be incorporated into various types of orthopedic implants. Such orthopedic implants may be for securing a prosthetic device implanted into bone, may be for the purpose of healing bone portions or for achieving fusion of bones, or for stabilizing a device to space apart and allow motion between the adjacent bones or bone portions. Such orthopedic implants may comprise any artificial or naturally occurring material appropriate for the intended purpose. Such materials would include, but are not limited to, implant quality metals, including, but not limited to, titanium and its alloys, surgical grade plastics and plastic composites which may or may not be bioresorbable, ceramics, and cortical bone. Some examples of interbody orthopedic implants that may benefit from the present teaching, include but are not limited to any artificial joint component having an intramedullary stem, such as but not limited to, hip replacements, shoulder replacements, knee replacements, and finger joints; and medical prosthetic implants for replacing a lost portion of a long bone.

BRIEF DESCRIPTION OF THE DRAWINGS

FIG. 1 is a top plan view of an orthopedic implant having a surface configuration in accordance with the present invention.

FIG. 2 is a side elevation view of the orthopedic implant of FIG. 1.

FIG. 3 is a side elevation view of the interbody orthopedic implant of FIG. 1 installed in an implantation site formed in bone shown in partial cross-section.

FIG. 8 is an enlarged fragmentary top plan view of a second embodiment of the implant surface of the present invention from a view taken along area 8 of FIG. 1.

FIG. 9 is a fragmentary side elevation view of the implant surface of FIG. 8 from a view taken along area 9 of FIG. 2.

FIG. 10 is a fragmentary end view of the implant surface of FIG. 8.

FIG. 11 is a fragmentary perspective view of the implant surface of FIG. 8.

FIG. 12 is an enlarged fragmentary top plan view of a third embodiment of the implant surface of the present invention from a view taken along area 12 of FIG. 1.

FIG. 14 is a fragmentary end view of FIG. 12.

FIG. 16 is an enlarged fragmentary top plan view of a fourth embodiment of the implant surface of the present invention from a view taken along area 16 of FIG. 1.

FIG. 17 is a fragmentary side elevation view of the implant surface of FIG. 16 from a view taken along area 17 of FIG. 2.

FIG. 18 is a fragmentary end view of FIG. 16.

FIG. 19A is an enlarged fragmentary perspective view of the implant surface of FIG. 16.

FIG. 19B is an enlarged fragmentary perspective view of a variation on the second and third surface projections of the fourth embodiment of the implant surface of the present invention with a cleave therethrough.

FIG. 20 is an enlarged fragmentary top plan view of a fifth embodiment of the implant surface of the present invention from a view taken along area 20 of FIG. 1.

FIG. 21 is a fragmentary side elevation view of the implant surface of FIG. 20 from a view taken along line 21 of FIG. 2.

FIG. 22 is a fragmentary end view of FIG. 20.

FIG. 23 is an enlarged fragmentary perspective view of the implant surface of FIG. 20.

DETAILED DESCRIPTION OF THE DRAWINGS

Figure 6:
FIG. 6 is a fragmentary end elevation view of FIG. 4.
Figure 4:
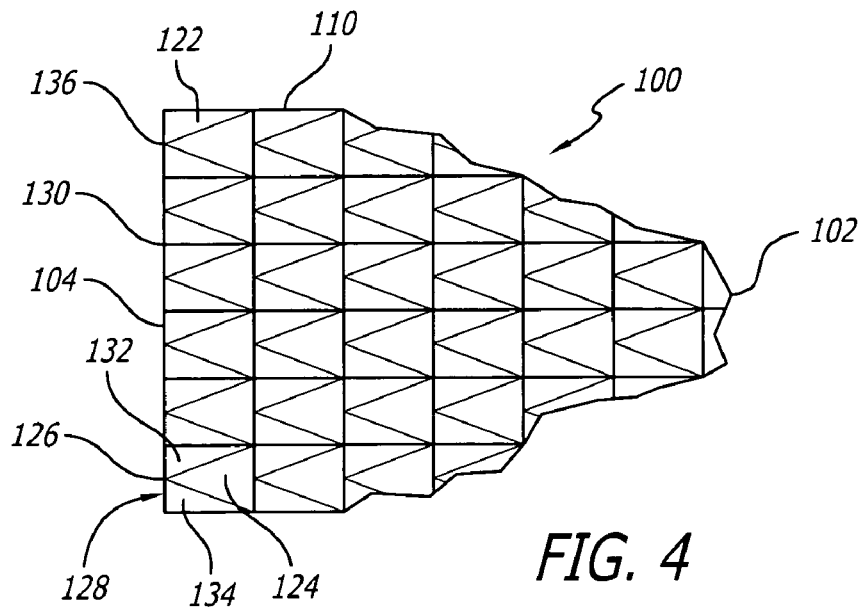
FIG. 4 is an enlarged fragmentary top plan view of an implant surface of one embodiment of the present invention from a view taken along area 4 of FIG. 1.
Figure 5:
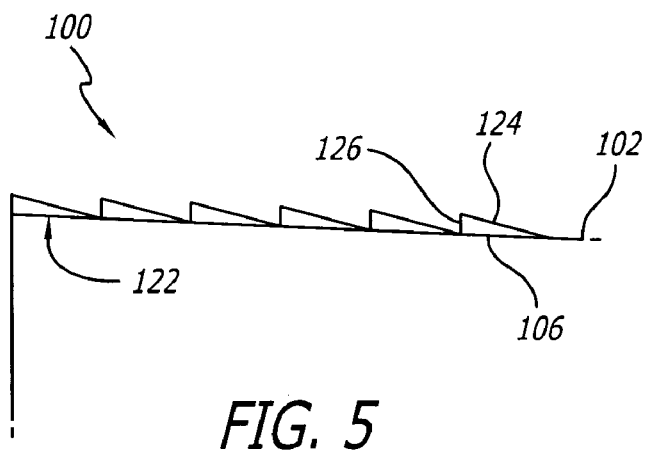
FIG. 5 is a fragmentary side elevation view of the implant surface of FIG. 4 from a view taken along area 5 of FIG. 2.
Figure 7:
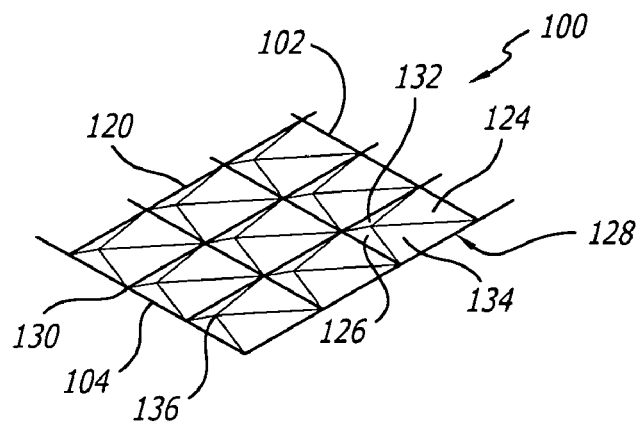
FIG. 7 is a fragmentary perspective view of the implant surface of FIG. 4.

As shown in FIGS. 1-7, an orthopedic implant 100, in the form of a hip prosthesis in this example, has a leading end 102, a trailing end 104, and an exterior surface 106. Implant 100 may converge from trailing end 104 to leading end 102 along a longitudinal axis L of implant 100 as shown, or may diverge, be parallel, or any combination thereof. Exterior surface 106 is configured to be placed against and in contact or engagement with the bone B, including adjacent bones or bone portions, of a human skeleton. It is appreciated that the surface configuration of the present invention is not limited to a hip prosthesis and may be incorporated in other types of orthopedic implants including such implants placed between adjacent bones or adjacent bone portions of the human skeleton. Exterior surface 106 may include large and/or small openings 114,116 to permit bone growth into and through implant 100. Exterior surface 106 of implant 100 can be generally planar, or can be arcuate as shown in the Figures, or any other configuration suitable for the desired use.

As shown in detail in FIGS. 4-7, at least a portion of exterior surface 106 of implant 100 has a surface configuration generally referred to by the numeral 120. In accordance with a first embodiment of the present invention, surface configuration 120 includes surface projections 122 configured to facilitate insertion of implant 100 into an implantation site while resisting expulsion of implant 100 in a direction opposite to the direction of insertion. Each of surface projections 122 has an angled forward facet 124 directed at least in part toward leading end 102 of implant 100 and a rearward facet 126 directed at least in part toward trailing end 104 of implant 100. Forward facet 124 has a length greater than the length of rearward facet 126. Rearward facet 126 has a slope that is steeper than the slope of forward facet 124. In this embodiment, the base of rearward facet 126 forms an angle of approximately 90 degrees with respect to exterior surface 106 of implant 100. It is appreciated that the angle of the base of rearward facet 126 with respect to exterior surface 106 of implant 100 may be perpendicular to, greater than perpendicular to, or less than perpendicular to the base of the surface where the facet arises. Forward facet 124 forms an angle in the range of approximately 10 to 60 degrees, with 25-45 degrees being preferred, with respect to exterior surface 106. Each one of surface projections 122 also has a left side facet 132 and a right side facet 134 directed toward the sides of implant 100.

In this embodiment of surface configuration 120, a plurality of surface projections 122 are spaced apart laterally (side to side) by longitudinal grooves 130 formed along the longitudinal axis L of implant 100. In one embodiment, longitudinal grooves 130 have a V-shaped horizontal cross-section. The lower most portions of left and right side facets 132, 134 of consecutive side-by-side projections 122 can be coincident with each other or may be spaced apart, any space therebetween can be at least in part flat, curved, sloped or otherwise configured. Each surface projection 122 has left and right side facets 132, 134 that converge to form a high point or peak 136 at the top of each surface projection 122. Each peak 136 can be aligned along lines that are perpendicular, parallel, and/or diagonally oriented to longitudinal axis L of implant 100. The left and right side facets 132, 134 resist side-to-side motion of implant 100 after it is inserted into the implantation space. Peaks 136 engage the bone B adjacent to implant 100 in the implantation site. It is appreciated that in a variation of the present invention, the peaks may be modified such as to be truncated or cut off to have a broader rather than shaper upper most surface. Moreover, the peaks can be cleaved in one or more directions so as to increase the surface area useful for engaging bone. The relieved areas of the cleaved projections are useful for containing and carrying fusion promoting substances other than bone such as bone morphogenetic proteins and genetic materials coding for the production of bone, or bone itself which could by way of example be in the form of a paste. It is further appreciated that for all the various embodiments of the surface configuration of the present invention, longitudinal grooves 130 can have horizontal cross-sections in a variety of configurations such as, without limitation, square-shaped or U-shaped configurations.

Sequential projections can be positioned on an implant wherein each surface projection has forward facing facets facing the same direction such that consecutive projections are oriented forward facing facet to rearward facing facet. The lower most portion of the slope of the forward facing facet of a first surface projection in a sequence can be coincident with the rearward facet of the next surface projection in the sequence. Alternatively, the forward facet of a first surface projection and the rearward facet of the next surface projection in a sequence can be spaced apart and the space can be at least in part flat, curved, or any other surface configuration suitable for the intended use. The surface projections can be oriented relative to one another to form an array and are preferably geometrically disposed relative to one another in a pattern wherein at least a portion of the projection is aligned along a longitudinal, horizontal, diagonal, or curved line. Further, it is appreciated that the surface of the present invention can be useful with orthopedic implants of various configurations, including configurations wherein at least one of leading end, trailing end, and sides of the orthopedic implant is curved. By way of example and not limitation, the leading end, trailing end, and sides of the orthopedic implant can form an oval, an oblong, a circle, or other geometric shape.

As shown in FIGS. 8-11, a second embodiment of the surface configuration of the present invention is generally referred to by the numeral 220. Surface configuration 220 includes surface projections 222 to facilitate insertion of implant 100 into an implantation site while resisting expulsion of implant 100 in a direction opposite to the direction of insertion. Each of surface projections 222 has an angled forward facet 224 directed at least in part toward leading end 202 of implant 100 and a rearward facet 226 directed at least in part toward trailing end 204 of implant 100. Forward facet 224 has a length greater than the length of rearward facet 226. Rearward facet 226 has a slope that is steeper than the slope of forward facet 224. In this embodiment, the base of rearward facet 226 forms an angle of approximately 45 degrees with respect to exterior surface 206 of implant 100. Each one of surface projections 222 has a left side facet 232 and a right side facet 234 directed toward the sides of implant 100, and forward facet 224 and rearward facet 226.

In this embodiment of surface configuration 220, longitudinal grooves 230 have a V-shaped horizontal cross-section. The lower most portions of left and right side facets 232, 234 of consecutive side-by-side projections 222 can be coincident with each other or may be spaced apart, any space therebetween can be at least in part flat, curved, sloped or otherwise configured. Each surface projection has left and right side facets 232, 234 that converge to form a high point or peak 236 at the top of each surface projections 222. Each peak 236 can be aligned along lines that are perpendicular, parallel, and/or diagonally oriented to the longitudinal axis L of implant 100. The left and right side facets 232, 234 resist side-to-side motion of implant 100 after it is inserted into the implantation space. Peaks 236 engage bone B adjacent to implant 100 in the implantation site.

Figure 13:
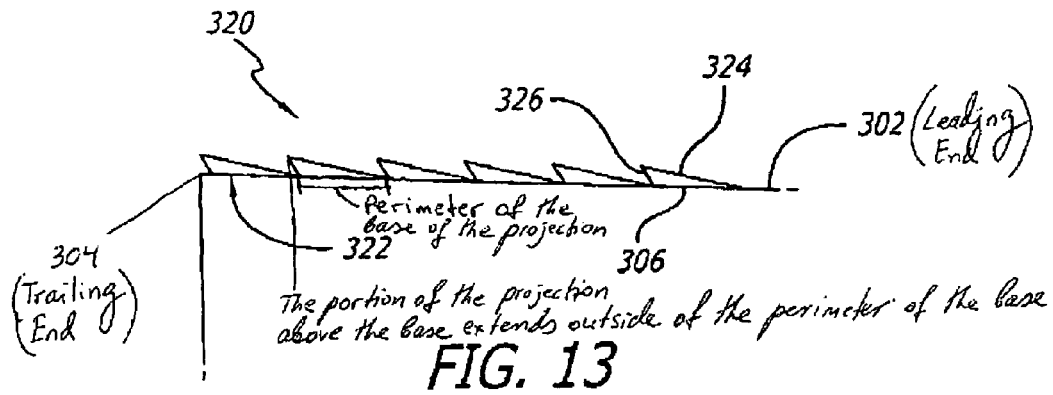
FIG. 13 is a fragmentary side elevation view of the implant surface of FIG. 12 from a view taken along area 13 of FIG. 2.
Figure 15:
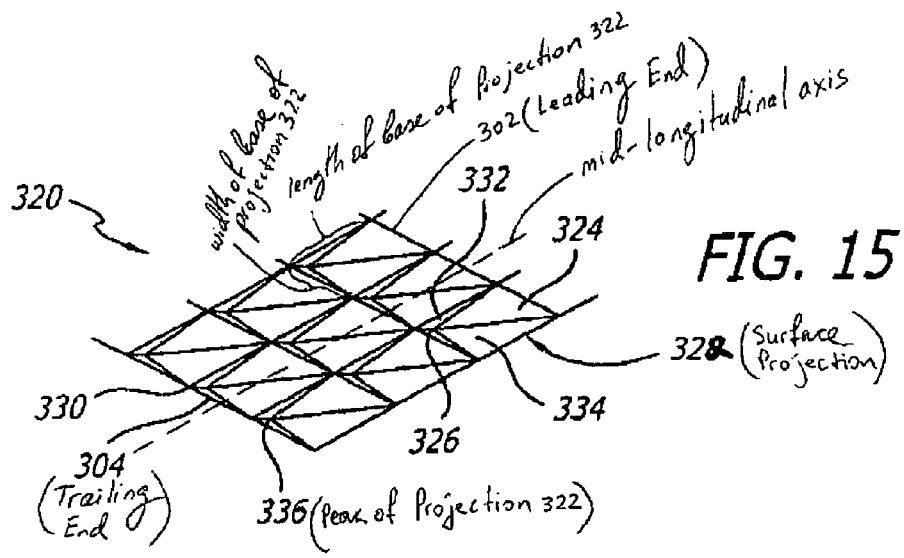
FIG. 15 is a fragmentary perspective view of the implant surface of FIG. 12.
Figure 24A:
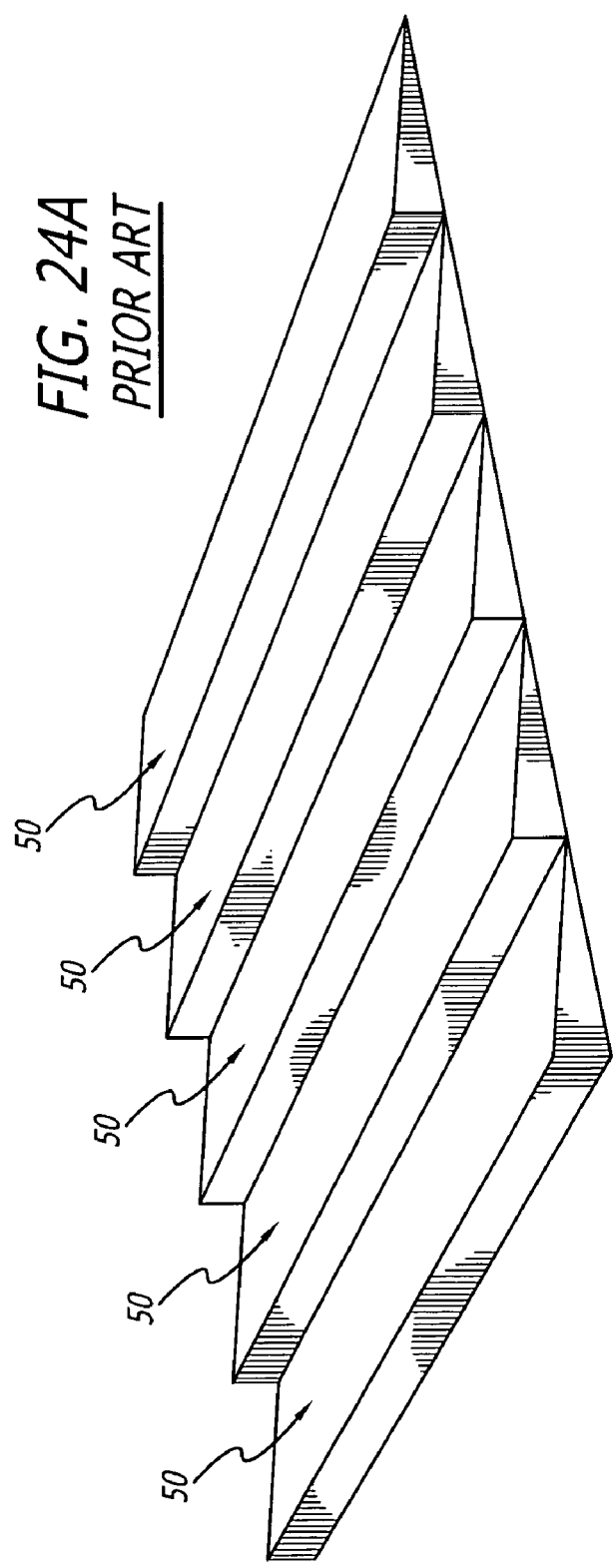
FIGS. 24A and 24B are perspective and side elevation views, respectively, of a prior art implant surface having forward facing ratchetings.
Figure 24B:
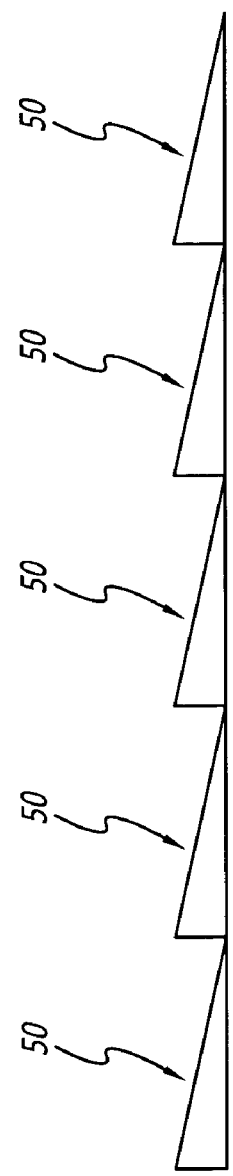

As shown in FIGS. 12-15, a third embodiment of the surface configuration of the present invention is generally referred to by the numeral 320 is shown. Surface configuration 320 includes surface projections 322 to facilitate insertion of implant 100 into an implantation site while resisting expulsion of implant 100 in a direction opposite to the direction of insertion. Each of surface projections 322 has an angled forward facet 324 directed at least in part toward leading end 302 of implant 100 and a rearward facet 326 directed at least in part toward trailing end 304 of implant 100. Forward facet 324 has a length greater than the length of rearward facet 326. Rearward facet 326 has a slope that is steeper than the slope of forward facet 324. In this embodiment, the base of rearward facet 326 is "back cut" to form an angle greater than 90 degrees with respect to exterior surface 306 of implant 100. The configuration of rearward facet 326 further enhances resistance of motion of the implant in a direction opposite to the direction of insertion. It is appreciated that the angle of the base of rearward facet 326 with respect to exterior surface 306 of implant 100 can be any other angle suitable for the intended purpose of the present invention. Each one of surface projections 322 has a left side facet 332 and a right side facet 334 directed toward the sides of implant 100, and a forward facet 324 and a rearward facet 326.

In this embodiment of surface configuration 320, longitudinal grooves 330 have a V-shaped horizontal cross section. The lower most portions of left and right side facets 332, 334 of consecutive side-by-side projections 322 can be coincident with each other or may be spaced apart, and any space therebetween can be at least in part flat, curved, sloped or otherwise configured. Each surface projection 322 has left and right side facets 332, 334 that converge to form a high point or peak 336 at the top of each surface projection 322. Each peak 336 can be aligned along lines that are perpendicular, parallel, and/or diagonally oriented to the longitudinal axis L of implant 100. The left and right side facets 332, 334 resist side-to-side motion of implant 100 after it is inserted into the implantation space. Peaks 336 engage bone B adjacent to implant 100 in the implantation site.

As shown in FIGS. 16-19B, a fourth embodiment of the surface configuration of the present invention is generally referred to by the numeral 420. Surface configuration 420 includes surface projections 422 configured to facilitate insertion of implant 100 in the direction of insertion into an implantation site while resisting expulsion of implant 100 in a direction opposite to the direction of insertion. Each of surface projections 422 has an angled forward facet 424 directed toward leading end 402 of implant 100 and a rearward portion 426 directed toward trailing end 404 of implant 100. Forward facet 424 has a length greater than the length of rearward portion 426. Rearward portion 426 has a slope that is steeper than the slope of forward facet 424. In this embodiment, the base of rearward portion 426 forms an angle of approximately 90 degrees with respect to exterior surface 406 of implant 100. Rearward portion 426 can be a portion of surface projection 422, such as a facet, an edge, or a line for example. Each one of surface projections 422 has a left side forward facet 450, a right side forward facet 452, a left side rearward facet 454, and a right side rearward facet 456 directed toward the front and sides, and directed toward the rear and sides of implant 100, respectively, and forward facet 424 and rearward portion 426.

Surface configuration 420 can further include a second plurality of surface projections 460 having at least a left forward side facet 462 and a right forward side facet 464 directed at least in part toward leading end 402 and sides of implant 100, respectively, and at least one rearward facet 466 directed at least in part toward trailing end 400. Left and right forward side facets 462, 464 have at least a first portion in a plane at an angle to the longitudinal axis of implant 100. Second surface projections 460 can be interspersed with surface projections 422.

Surface configuration 420 can further comprise a third plurality of surface projections 470 having at least a left rearward side facet 472 and a right rearward side facet 474 directed at least in part toward trailing end 404 and sides of implant 100, respectively, and at least one forward facet 476 directed at least in part toward leading end 402. Left and right rearward side facets 472, 474 have at least a first portion in a plane at an angle to the longitudinal axis of implant 100. Third surface projections 470 can be interspersed with surface projections 422 and/or second surface projections 460. Surface projections 422 may have a length approximating the combined length of second surface projections 460 and third surface projections 470.

In this embodiment, surface configuration 420 has angled grooves 440a-k that form a plurality of surface projections 422. In this example, angled grooves 440a-k are formed at an angle that is approximately 45 degrees to longitudinal axis L of orthopedic implant 100 and in this example, angled grooves 440a-k are approximately 90 degrees to one another. The angled grooves 440a-k can be formed, if machined, by first passing a cutting element at a 45 degree angle to the longitudinal axis L of implant 100 and then passing the cutting element at a 90 degree angle to the path of the first pass of the cutting element, or otherwise formed by casting, molding, and other methods for forming a surface configuration. It is appreciated that angled grooves 400a-k can be formed at various angles to the longitudinal axis L of implant 100 and to each other. For example, such angles can be less than 180 degrees.

In this embodiment of surface configuration 420, angled grooves 440a-k have a V-shaped horizontal cross-section. Each surface projection 422 has left and right side facets 432 and 434 that are convergent and form a high point or peak 436 at the top of each surface projections 422. Each peak 436 can be aligned along lines that are horizontally, longitudinally, and/or diagonally oriented along implant 100. The left and right side forward and rearward facets 450, 452, 454, 456 function to prevent side-to-side motion of implant 100 after it is inserted into the implantation space. Peaks 436 may also function like teeth to engage bone B adjacent to the implant in the implantation site.

FIG. 19B shows a variation of second and third surface projections 460', 470' that can be cleaved in one or more directions to increase the number of exposed sides of each projection and thus increase the surface area of the implant bone engaging surface available to contact bone B. A preferred embodiment of this variation of the second and third surface projections 460', 470' are cleaved by a longitudinal groove.

As shown in FIGS. 20-23, a fifth embodiment of the surface configuration of the present invention is generally referred to by the numeral 520. Surface configuration 520 includes surface projections 522 to facilitate insertion of implant 100 into an implantation site while resisting expulsion of implant 100 in a direction opposite to the direction of insertion. Surface projections 522 can be cleaved in one or more directions to increase the number of exposed sides of each projection and thus increase the surface area of the implant bone engaging surface available to contact bone B. For example, the surface projections can be cleaved by a longitudinal cut 540 generally parallel to the longitudinal axis L of implant 100 to form a surface projection having nine exposed sides. The surface projections may further be cleaved by a horizontal cut 542 generally perpendicular to the longitudinal axis L of implant 100 to form a surface projection having eighteen exposed sides. The cuts can penetrate the surface projection at a depth substantially equal to that of the height of the surface projections as measured from the upper or lower surfaces of the implant. The cuts can be oriented along at least one of the longitudinal axis of the implant, an axis perpendicular to the longitudinal axis of said implant, and an axis at an angle between the longitudinal axis and the axis perpendicular to the longitudinal axis of the implant. It is appreciated that cuts 540 and 542 may be formed as part of the molding process for forming the surface projections.

When cleaved by longitudinal cut 540 and horizontal cut 542, each of surface projections 522 has angled forward facet 524a, 524b directed at least in part toward leading end 502 of implant 100 and rearward facets 526a, 526b directed at least in part toward trailing end 504 of implant 100. Forward facet 524 has a length greater than the length of rearward facet 526. Rearward facets 526a, 526b have a slope that is steeper than the slope of forward facets 524a, 524b. The cleaved portion of surface projection 522 can be spaced apart by a predetermined distance and the space can be at least in part flat, curved, or any other surface configuration suitable for the intended use. In this embodiment, the base of rearward facets 526a, 526b forms an angle of approximately 45 degrees with respect to exterior surface 506 of implant 100. Each one of surface projections 522 has left side facets 532a, 532b and right side facets 534a, 534b directed toward the sides of implant 100, and forward facets 524a, 524b and rearward facet 526a, 526b. In this embodiment of surface configuration 520, longitudinal grooves 530 have a V-shaped horizontal cross-section and each surface projection 522 has left and right side facets 532a, 532b, 534a, 534b that converge toward one another. The left and right side facets 532a, 532b, 534a, 534b resist side-to-side motion of implant 100 after it is inserted into the implantation space.

The surface configuration of the present invention can be formed by molding, machining or otherwise. A preferred surface configuration of the present invention may readily be machined by milling from side to side, across the bone engaging surfaces, surface projections. A milling machine with a cutting tool having an angled cutting face such as a V-shaped profile can then be run through the plurality of surface projections parallel to the longitudinal axis of the implant to form the above-described surface. In a preferred embodiment, the V-shaped cutting tool of the milling machine has faces with an angle of approximately 90 degrees, which faces are at a 45-degree angle to the plane of the surfaces being so machined. Without departing from the present invention, the angle of the cutting faces can be more or less than 90 degrees, the angle of the cutting face to the surface to be cut can be more or less than 45 degrees, and rather than running the cutter element parallel to the longitudinal axis of the implant, the cutting element may be run at an angle. By way of example only and not limitation, this angle may be at 45 degrees to the longitudinal axis of the implant and each surface projection can be formed by two grooves crossing the projections at a 90 degree angle to each other.

The orthopedic implants of the present invention are made of artificial or naturally occurring materials suitable for implantation in the human body. The implants can comprise bone including, but not limited to, cortical bone, materials other than bone, such as metals including, but not limited to, titanium and its alloys or ASTM material, surgical grade plastics, plastic composites, ceramics, or other materials suitable for use as an orthopedic implant. The implants of the present invention can further comprise or be combined with bone growth promoting materials, including but not limited to, bone, bone morphogenetic proteins, hydroxyapatite, and genes coding for the production of bone. The implants can be treated with a bone growth promoting substance, can be a source of osteogenesis, or can be bioabsorbable at least in part. The implants of the present invention can be formed of a porous material.

The orthopedic implants of the present invention can be for the purpose of achieving fusion. The exterior surface of the fusion implants can include at least one opening to permit for the growth of bone from bone or bone portion to adjacent bone or bone portion through the implant. The implant can have an internal chamber and may also have an access opening for accessing the internal chamber, in which case the implant can further have a cover such as a cap to close the access opening at least in part. Openings in the exterior surface of the implant can communicate with the internal chamber to permit further growth of bone through the implant. The internal chamber can contain bone growth promoting materials, including but not limited to, bone, bone morphogenetic proteins, hydroxyapatite, and genes coding for the production of bone. The implants of the present invention can be formed of a material that intrinsically participates in the growth of bone from one of the adjacent bones or bone portions to the other of the adjacent bones or bone portions.

While various embodiments of the present invention are presented by way of example only and not limitation, common to each of them, is that the configuration of the surface is based on a plurality of surface projections disposed in arrays, each surface projection comprising at least one leading facet and at least one opposing trailing facet, in which the leading facet has a length greater than the trailing facet and the trailing facet has a steeper slope than the slope of the leading facet. The surface configuration is located on at least a portion of exterior bone engaging surface of the orthopedic implant.

While the implant shown in FIGS. 1, 2, and 3 is a hip prosthesis, it is appreciated that the surface configuration of the present invention is applicable to any orthopedic implants having an exterior surface incorporating the present inventive teachings for engaging bone including but not limited to, any artificial joint component having an intramedullary stem, such as but not limited to, hip replacements, shoulder replacements, knee replacements, and finger joints; and medical prosthetic implants for replacing a lost portion of a long bone.

It is believed that the operation and construction of the present invention will be apparent from the foregoing description and, while the invention shown and described herein has been characterized as particular embodiments, changes and modifications may be made therein without departing from the spirit and scope of the invention as defined in the following claims.

What is claimed is:

1. An orthopedic implant for contact with bone, including adjacent bones and adjacent bone portions, of a human skeleton, said implant comprising:
a leading end for introduction of said orthopedic implant into the bone, an opposite trailing end, spaced apart sides therebetween, and a mid-longitudinal axis passing through said leading and trailing ends;
an exterior surface between said leading and trailing ends and said spaced apart sides, said exterior surface adapted for placement in engagement with the bone; and
a plurality of surface projections formed on said exterior surface of said implant, at least a first and a second of said surface projections each having at least one forward facing facet directed at least in part toward said leading end and at least one rearward facet directed at least in part toward said trailing end, each of said forward facet and rearward facet having a length and a slope, the length of said forward facet being longer than the length of said rearward facet, the slope of said rearward facet being steeper than the slope of said forward facet, the slope of said forward facets of said at least said first and said second of said surface projections being the same, at least a portion of said rearward facet of said first surface projection overlying a portion of said forward facet of said second surface projection, said first and second surface projections each having opposed side facets directed generally toward said spaced apart sides of said implant, respectively, said side facets being located between said forward facet and said rearward facet of each of said first and second surface projections.

2. The orthopedic implant of claim 1, wherein said rearward facet is at an angle to said exterior surface of said implant.

3. The orthopedic implant of claim 2, wherein the angle is greater than 90 degrees.

4. The orthopedic implant of claim 1, wherein said surface projections are oriented relative to one another to form an array.

5. The orthopedic implant of claim 1, wherein said surface projections are geometrically disposed relative to one another.

6. The orthopedic implant of claim 1, wherein said exterior surface of said implant is at least in part arcuate.

7. The orthopedic implant of claim 1, wherein at least one of said leading end, trailing end, and sides are curved.

8. The orthopedic implant of claim 1, wherein said sides are curved.

9. The orthopedic implant of claim 1, wherein each of said leading end, trailing end, and sides are curved.

10. The orthopedic implant of claim 9, wherein said leading end, trailing end, and sides form a circle.

11. The orthopedic implant of claim 1, wherein exterior surface of said implant is at least in part planar.

12. The orthopedic implant of claim 1, wherein said implant is tapered along at least a portion of the length of said implant.

13. The orthopedic implant of claim 1, wherein said implant comprises a material other than bone.

14. The orthopedic implant of claim 1, wherein said implant comprises bone.

15. The orthopedic implant of claim 14, wherein said bone includes cortical bone.

16. The orthopedic implant of claim 1, wherein said implant comprises bone growth promoting material.

17. The orthopedic implant of claim 16, wherein said bone growth promoting material is one of bone morphogenetic protein, hydroxyapatite, and genes coding for the production of bone.

18. The orthopedic implant of claim 1, wherein said implant is treated with a bone growth promoting substance.

19. The orthopedic implant of claim 1, wherein said implant is a source of osteogenesis.

20. The orthopedic implant of claim 1, wherein said implant is at least in part bioabsorbable.

21. The orthopedic implant of claim 1, wherein said implant comprises metal.

22. The orthopedic implant of claim 21, wherein said metal is ASTM material suitable for use as an orthopedic implant.

23. The orthopedic implant of claim 21, wherein said metal includes titanium.

24. The orthopedic implant of claim 1, wherein said implant comprises a plastic material.

25. The orthopedic implant of claim 1, wherein said implant comprises a ceramic material.

26. The orthopedic implant of claim 1, wherein said implant is formed of a porous material.

27. The orthopedic implant of claim 1, wherein said implant is formed of a material that intrinsically participates in the growth of bone from adjacent bone to adjacent bone through said implant.

28. The orthopedic implant of claim 1, wherein said implant is a motion preserving device adapted to space apart and allow motion between the adjacent bone or bone portions.

29. The orthopedic implant of claim 1, wherein said orthopedic implant is a fusion implant.

30. The orthopedic implant of claim 29, wherein said exterior surface includes at least one opening to permit bone growth from adjacent bone to adjacent bone through said implant.

31. The orthopedic implant of claim 29, wherein said implant has an internal chamber and an access opening for accessing said internal chamber.

32. The orthopedic implant of claim 31, wherein said implant has a cap for closing said access opening.

33. The orthopedic implant of claim 31, wherein said exterior surface includes at least one opening in communication with said internal chamber to permit bone growth from adjacent bone to adjacent bone through said implant.

34. The orthopedic implant of claim 31, wherein said internal chamber is capable of containing bone growth promoting material.

35. The orthopedic implant of claim 34, wherein said bone growth promoting material is one of bone morphogenetic protein, hydroxyapatite, and genes coding for the production of bone.

36. The orthopedic implant of claim 1 further comprising at least one opening capable of retaining fusion promoting materials.

37. The orthopedic implant of claim 1, further comprising at least one cut cleaving said surface projection into at least two portions.

38. The orthopedic implant of claim 37, further comprising at least a second cut cleaving said surface projection into at least four portions.

39. The orthopedic implant of claim 37, where said cut penetrates said surface projection at a depth substantially equal to that of the height of said surface projection.

40. The orthopedic implant of claim 38, where said second cut penetrates said surface projection at a depth substantially equal to that of the height of said surface projection.

41. The orthopedic implant of claim 37, wherein said cut is oriented along one of the mid-longitudinal axis of said implant, an axis perpendicular to the mid-longitudinal axis of said implant, and an axis at an angle between the mid-longitudinal axis and the axis perpendicular to the mid-longitudinal axis of said implant.

42. The orthopedic implant of claim 1, in combination with a fusion promoting substance.

43. The orthopedic implant of claim 42, wherein said fusion promoting substance includes at least one of bone, bone morphogenetic protein, hydroxyapatite, and genes coding for the production of bone.

44. The orthopedic implant of claim 1, wherein each of said first and second surface projections have a base that is adjacent to one another.

45. The orthopedic implant of claim 1, wherein each of said first and second surface projections have a base, the bases being spaced apart from one another along a direction generally parallel to the mid-longitudinal axis of said implant.

46. The orthopedic implant of claim 1, wherein each of said first and second surface projections have a base, the bases being spaced apart from one another along a direction generally transverse to the mid-longitudinal axis of said implant.

47. The orthopedic implant of claim 1, wherein said side facets converge toward each other in a direction away from said exterior surface of said implant.

48. The orthopedic implant of claim 47, wherein said opposed side facets intersect each other.

49. The orthopedic implant of claim 48, wherein said opposed side facets converge to form a peak at the top of said surface projection.

50. The orthopedic implant of claim 49, wherein said peaks of at least two of said surface projections are aligned along lines that are at least one of perpendicular, parallel, and diagonal to the mid-longitudinal axis of said implant.

51. The orthopedic implant of claim 49, wherein said peak of said first surface projection overlies at least a portion of said second surface projection.

52. The orthopedic implant of claim 49, wherein said peaks of said first and second surface projections are at the same height above said exterior surface of said implant.

53. The orthopedic implant of claim 1, wherein adjacent side facets of adjacent surface projections are spaced apart to define a groove therebetween.

54. The orthopedic implant of claim 1, wherein a plurality of adjacent surface projections are spaced apart to form a plurality of grooves therebetween.

55. The orthopedic implant of claim 54, wherein at least one of said grooves is parallel to the mid-longitudinal axis of said implant.

56. The orthopedic implant of claim 54, wherein at least two of said grooves cross each other.

57. The orthopedic implant of claim 54, wherein at least one of said grooves has a horizontal cross-sectional shape that is one of a v-shape, u-shape, and a box-like shape.

58. The orthopedic implant of claim 1, wherein each of said first and second surface projections have a base and said side facets have a maximum width therebetween at the base, the base being spaced apart from a base of another of said surface projections by a distance no greater than one-half the maximum width of one of said first and second surface projections.

59. The orthopedic implant of claim 1, wherein said forward facets of each of said first and second surface projections face the same direction.

60. An orthopedic implant for contact with bone, including adjacent bones and bone portions, of a human skeleton, said implant comprising:
a leading end, an opposite trailing end, a mid-longitudinal axis passing through said leading and trailing ends, and right and left sides between said leading and trailing ends, said right and left sides being spaced apart on opposite sides of the mid-longitudinal axis and;
an exterior surface between said leading and trailing ends and said right and left sides, said exterior surface adapted for placement in engagement with the bone; and
a plurality of surface projections formed on said exterior surface of said implant, each of said surface projections having a plurality of facets, each of said facets having a perimeter defining each facet, at least a first and a second of said surface projections each having at least a first facet and at least a second facet opposite said first facet, each of said first and second facets having a length and a slope, the length of said first facet being longer than the length of said second facet, the slope of said second facet being steeper than the slope of said first facet, said second facet including a perimeter having at least a first and a second portion arranged to form an apex having an included angle greater than 90 degrees between said first and second portions of the perimeter.

61. The orthopedic implant of claim 60, wherein said second facet is at an angle to said exterior surface of said implant.

62. The orthopedic implant of claim 61, wherein the angle is greater than 90 degrees.

63. The orthopedic implant of claim 60, wherein said projections are oriented relative to one another to form an array.

64. The orthopedic implant of claim 60, wherein said projections are geometrically disposed relative to one another.

65. The orthopedic implant of claim 60, wherein said exterior surface of said implant is at least in part arcuate.

66. The orthopedic implant of claim 60, wherein said exterior surface of said implant is at least in part planar.

67. The orthopedic implant of claim 60, wherein said implant is tapered along at least a portion of the length of said implant.

68. The orthopedic implant of claim 60, wherein said implant comprises bone growth promoting material.

69. The orthopedic implant of claim 68, wherein said bone growth promoting material is one of bone morphogenetic protein, hydroxyapatite, and genes coding for the production of bone.

70. The orthopedic implant of claim 60, wherein said implant is a motion preserving device adapted to space apart and allow motion between the adjacent bone or bone portions.

71. The orthopedic implant of claim 60, wherein said orthopedic implant is a fusion implant.

72. The orthopedic implant of claim 60, in combination with a fusion promoting substance.

73. The orthopedic implant of claim 72, wherein said fusion promoting substance includes at least one of bone, bone morphogenetic protein, hydroxyapatite, and genes coding for the production of bone.

74. The orthopedic implant of claim 60, wherein each of said first and second surface projections have a base, the bases being adjacent to one another.

75. The orthopedic implant of claim 60, wherein each of said first and second surface projections have a base, the bases being spaced apart from one another along a direction generally parallel to the mid-longitudinal axis of said implant.

76. The orthopedic implant of claim 60, wherein each of said first and second surface projections have a base, the bases being spaced apart from one another along a direction generally transverse to the mid-longitudinal axis of said implant.

77. The orthopedic implant of claim 60, wherein said first and second surface projections each have a base and opposed side facets directed generally toward said leading and trailing ends, respectively, said side facets being located between said first facet and said second facet of each of said first and second surface projections, said side facets converging toward each other in a direction away from the base of each of said first and second surface projections.

78. The orthopedic implant of claim 77, wherein adjacent side facets of adjacent surface projections are spaced apart to define a groove therebetween.

79. The orthopedic implant of claim 77, wherein said side facets have a maximum width therebetween at the base of said first and second surface projections, the base being spaced apart from a base of another of said surface projections by a distance no greater than one-half the maximum width of one of said first and second surface projections.

80. The orthopedic implant of claim 77, wherein said opposed side facets converge to form a peak, said peaks of said first and second surface projections being at the same height above said exterior surface of said implant.

81. The orthopedic implant of claim 60, wherein said at least one first facet of each of said first and second surface projections face the same direction.

82. An orthopedic implant for contact with bone, including adjacent bones and bone portions, of a human skeleton, said implant comprising:
a leading end for introduction of said orthopedic implant into the bone, an opposite trailing end, spaced apart sides therebetween, and a mid-longitudinal axis passing through said leading and trailing ends;
an exterior surface between said leading and trailing ends and said spaced apart sides, said exterior surface adapted for placement in engagement with the bone; and
a plurality of surface projections formed on said exterior surface of said implant, at least a first and a second of said surface projections each having at least one forward facing facet directed at least in part toward said leading end and at least one rearward facet directed at least in part toward said trailing end, each of said forward facet and rearward facet having a length and a slope, the length of said forward facet being longer than the length of said rearward facet, the slope of said rearward facet being steeper than the slope of said forward facet, said first and second surface projections each having a base and an included angle between said rearward facet and the base greater than 90 degrees relative to said exterior surface of said implant, said surface projections having opposed side facets directed generally toward said sides of said implant, said side facets being located between said forward facet and said rearward facet of said surface projections, said side facets converging toward each other in a direction away from the base of said first and second projections.

83. The orthopedic implant of claim 82, wherein said exterior surface of said implant is at least in part arcuate.

84. The orthopedic implant of claim 82, wherein at least one of said leading end, trailing end, and sides are curved.

85. The orthopedic implant of claim 82, wherein said sides are curved.

86. The orthopedic implant of claim 82, wherein each of said leading end, trailing end, and sides are curved.

87. The orthopedic implant of claim 86, wherein said leading end, trailing end, and sides form a circle.

88. The orthopedic implant of claim 82, wherein said exterior surface of said implant is at least in part planar.

89. The orthopedic implant of claim 82, wherein said implant is tapered along at least a portion of the length of said implant.

90. The orthopedic implant of claim 82, wherein said implant comprises a material other than bone.

91. The orthopedic implant of claim 82, wherein said implant comprises bone.

92. The orthopedic implant of claim 91, wherein said bone includes cortical bone.

93. The orthopedic implant of claim 82, wherein said implant comprises bone growth promoting material.

94. The orthopedic implant of claim 93, wherein said bone growth promoting material is one of bone morphogenetic protein, hydroxyapatite, and genes coding for the production of bone.

95. The orthopedic implant of claim 82, wherein said implant is treated with a bone growth promoting substance.

96. The orthopedic implant of claim 82, wherein said implant is a source of osteogenesis.

97. The orthopedic implant of claim 82, wherein said implant is at least in part bioabsorbable.

98. The orthopedic implant of claim 82, wherein said implant comprises metal.

99. The orthopedic implant of claim 98, wherein said metal includes titanium.

100. The orthopedic implant of claim 82, wherein said implant comprises at least one of a plastic material and a ceramic material.

101. The orthopedic implant of claim 82, wherein said implant is formed of a porous material and a material that intrinsically participates in the growth of bone from adjacent bone to adjacent bone through said implant.

102. The orthopedic implant of claim 82, wherein said implant is a motion preserving device adapted to space apart and allow motion between the adjacent bones and bone portions.

103. The orthopedic implant of claim 82, wherein said orthopedic implant is a fusion implant.

104. The orthopedic implant of claim 103, wherein said exterior surface includes at least one opening to permit bone growth from adjacent bone to adjacent bone through said implant.

105. The orthopedic implant of claim 103, wherein said implant has an internal chamber and an access opening for accessing said internal chamber.

106. The orthopedic implant of claim 105, wherein said exterior surface includes at least one opening in communication with said internal chamber to permit bone growth from adjacent bone to adjacent bone through said implant.

107. The orthopedic implant of claim 105, wherein said internal chamber is capable of containing bone growth promoting material.

108. The orthopedic implant of claim 107, wherein said bone growth promoting material is one of bone morphogenetic protein, hydroxyapatite, and genes coding for the production of bone.

109. The orthopedic implant of claim 82, further comprising at least one opening capable of retaining fusion promoting materials.

110. The orthopedic implant of claim 82, wherein the bases of said first and second surface projections are adjacent to one another.

111. The orthopedic implant of claim 82, wherein said opposed side facets converge to form a peak at the top of each of said surface projections.

112. The orthopedic implant of claim 111, wherein said peaks are aligned along lines that are at least one of perpendicular, parallel, and diagonal to the mid-longitudinal axis of said implant.

113. The orthopedic implant of claim 82, wherein adjacent side facets of adjacent surface projections are spaced apart to define a groove therebetween.

114. The orthopedic implant of claim 82, wherein a plurality of adjacent surface projections are spaced apart to form a plurality of grooves therebetween.

115. The orthopedic implant of claim 114, wherein at least one of said grooves is parallel to the mid-longitudinal axis of said implant.

116. The orthopedic implant of claim 114, wherein at least two of said grooves cross each other.

117. The orthopedic implant of claim 114, wherein at least one of said grooves has a horizontal cross-sectional shape that is one of a v-shape, u-shape, and a box-like shape.

118. An orthopedic implant for contact with bone, including adjacent bones and bone portions, of a human skeleton, said implant comprising:
a leading end for introduction of said orthopedic implant into the bone, an opposite trailing end, spaced apart sides therebetween, and a mid-longitudinal axis passing through said leading and trailing ends;
an exterior surface between said leading and trailing ends and said spaced apart sides, said exterior surface adapted for placement in engagement with the bone; and
a plurality of surface projections formed on said exterior surface of said implant, each of said surface projections having a forward facet directed at least in part toward said leading end and a rearward facet directed at least in part toward said trailing end, said rearward facet including a perimeter having at least a first and a second portion arranged to form an apex having an included angle greater than 90 degrees between said first and second portions.

119. The orthopedic implant of claim 118, wherein one of said facets is formed in the shape of a triangle having a vertex with an included angle greater than 90 degrees.

120. The orthopedic implant of claim 118, wherein each of said forward facet and said rearward facet of said first and second projections have a length and a slope, the length of said forward facet being longer than the length of said rearward facet, the slope of said rearward facet being steeper than the slope of said forward facet.

121. The orthopedic implant of claim 118, wherein said rearward facet is at an angle to said exterior surface of said implant.

122. The orthopedic implant of claim 121, wherein the angle is greater than 90 degrees.

123. The orthopedic implant of claim 118, wherein said surface projections are oriented relative to one another to form an array.

124. The orthopedic implant of claim 118, wherein said surface projections are geometrically disposed relative to one another.

125. The orthopedic implant of claim 118, wherein said exterior surface of said implant is at least in part arcuate.

126. The orthopedic implant of claim 118, wherein at least one of said leading end, trailing end, and sides are curved.

127. The orthopedic implant of claim 118, wherein said sides are curved.

128. The orthopedic implant of claim 118, wherein each of said leading end, trailing end, and sides are curved.

129. The orthopedic implant of claim 128, wherein said leading end, trailing end, and sides form a circle.

130. The orthopedic implant of claim 118, wherein said exterior surface of said implant is at least in part planar.

131. The orthopedic implant of claim 118, wherein said implant is tapered along at least a portion of the length of said implant.

132. The orthopedic implant of claim 118, wherein said implant comprises a material other than bone.

133. The orthopedic implant of claim 118, wherein said implant comprises bone.

134. The orthopedic implant of claim 133, wherein said bone includes cortical bone.

135. The orthopedic implant of claim 118, wherein said implant comprises bone growth promoting material.

136. The orthopedic implant of claim 135, wherein said bone growth promoting material is one of bone morphogenetic protein, hydroxyapatite, and genes coding for the production of bone.

137. The orthopedic implant of claim 118, wherein said implant is treated with a bone growth promoting substance.

138. The orthopedic implant of claim 118, wherein said implant is a source of osteogenesis.

139. The orthopedic implant of claim 118, wherein said implant is at least in part bioabsorbable.

140. The orthopedic implant of claim 118, wherein said implant comprises metal.

141. The orthopedic implant of claim 140, wherein said metal is ASTM material suitable for use as an orthopedic fusion implant.

142. The orthopedic implant of claim 140, wherein said metal includes titanium.

143. The orthopedic implant of claim 118, wherein said implant comprises a plastic material.

144. The orthopedic implant of claim 118, wherein said implant comprises a ceramic material.

145. The orthopedic implant of claim 118, wherein said implant is formed of a porous material.

146. The orthopedic implant of claim 118, wherein said implant is formed of a material that intrinsically participates in the growth of bone from adjacent bone to adjacent bone through said implant.

147. The orthopedic implant of claim 118, wherein said implant is a motion preserving device adapted to space apart and allow motion between the adjacent bone and bone portions.

148. The orthopedic implant of claim 118, wherein said orthopedic implant is a fusion implant.

149. The orthopedic implant of claim 148, wherein said exterior surface includes at least one opening to permit bone growth from adjacent bone to adjacent bone through said implant.

150. The orthopedic implant of claim 148, wherein said implant has an internal chamber and an access opening for accessing said internal chamber.

151. The orthopedic implant of claim 150, wherein said implant has a cap for closing said access opening.

152. The orthopedic implant of claim 150, wherein said exterior surface includes at least one opening in communication with said internal chamber to permit bone growth from adjacent bone to adjacent bone through said implant.

153. The orthopedic implant of claim 150, wherein said internal chamber is capable of containing bone growth promoting material.

154. The orthopedic implant of claim 153, wherein said bone growth promoting material is one of bone morphogenetic protein, hydroxyapatite, and genes coding for the production of bone.

155. The orthopedic implant of claim 118, further comprising at least one opening capable of retaining fusion promoting materials.

156. The orthopedic implant of claim 118, in combination with a fusion promoting substance.

157. The orthopedic implant of claim 156, wherein said fusion promoting substance includes at least one of bone, bone morphogenetic protein, hydroxyapatite, and genes coding for the production of bone.

158. The orthopedic implant of claim 118, wherein each of said first and second surface projections have a base, the bases being adjacent to one another.

159. The orthopedic implant of claim 118, wherein each of said first and second surface projections have a base, the bases being spaced apart from one another along a direction generally parallel to the mid-longitudinal axis of said implant.

160. The orthopedic implant of claim 118, wherein each of said first and second surface projections have a base, the bases being spaced apart from one another along a direction generally transverse to the mid-longitudinal axis of said implant.

161. The orthopedic implant of claim 118, wherein said forward facets of each of said first and second surface projections face the same direction.

162. The orthopedic implant of claim 118, wherein said first and second surface projections each have opposed side facets directed generally toward said spaced apart sides of said implant, respectively, said side facets being located between said forward facet and said rearward facet of each of said first and second surface projections, said side facets converging toward each other in a direction away from said exterior surface of said implant.

163. The orthopedic implant of claim 162, wherein said opposed side facets intersect each other.

164. The orthopedic implant of claim 163, wherein said opposed side facets converge to form a peak at the top of said surface projection.

165. The orthopedic implant of claim 164, wherein said peaks of at least two of said surface projections are aligned along lines that are at least one of perpendicular, parallel, and diagonal to the mid-longitudinal axis of said implant.

166. The orthopedic implant of claim 164, wherein said peak of said first surface projection overlies at least a portion of said second surface projection.

167. The orthopedic implant of claim 164, wherein said peaks of said first and second surface projections are at the same height above said exterior surface of said implant.

168. The orthopedic implant of claim 162, wherein adjacent side facets of adjacent surface projections are spaced apart to define a groove therebetween.

169. The orthopedic implant of claim 162, wherein a plurality of adjacent surface projections are spaced apart to form a plurality of grooves therebetween.

170. The orthopedic implant of claim 169, wherein at least one of said grooves is parallel to the mid-longitudinal axis of said implant.

171. The orthopedic implant of claim 169, wherein at least two of said grooves cross each other.

172. The orthopedic implant of claim 169, wherein at least one of said grooves has a horizontal cross-sectional shape that is one of a v-shape, u-shape, and a box-like shape.

173. The orthopedic implant of claim 162, wherein each of said first and second surface projections have a base and said side facets have a maximum width therebetween at the base, the base being spaced apart from a base of another of said surface projections by a distance no greater than one-half the maximum width of one of said first and second surface projections.

174. An interbody orthopedic implant for contact with bone including adjacent bones and bone portions, of a human skeleton, said implant comprising:

a leading end for introduction of said orthopedic implant into the bone, an opposite trailing end, spaced apart sides therebetween, and a mid-longitudinal axis passing through said leading and trailing ends;

an exterior surface between said leading and trailing ends and said spaced apart sides, said exterior surface adapted for placement in engagement with the bone; and a plurality of surface projections formed on said exterior surface of said implant, at least a first and a second of said surface projections each having at least one forward facing facet directed at least in part toward said leading end and at least one rearward facet directed at least in part toward said trailing end, each of said forward facet and rearward facet having a length and a slope, the length of said forward facet being longer than the length of said rearward facet, the slope of said rearward facet being steeper than the slope of said forward facet, said first and second surface projections each forming a base having a perimeter and a portion above the base, said base having a width and a length greater than width, the length extending along the mid-longitudinal axis of said implant, the width being transverse to the length, said portion above the base of said first and second surface projections extending outside of the perimeter of the base of a respective one of said first and second surface projections, said first and second surface projections each having opposed side facets directed generally toward said spaced apart sides of said implant, respectively, said side facets being located between said forward facet and said rearward facet of each of said first and second surface projections, said side facets converging toward each other in a direction away from said exterior surface of said implant.

175. The orthopedic implant of claim 174, wherein said rearward facet is at an angle to said exterior surface of said implant.

176. The orthopedic implant of claim 175, wherein the angle is greater than 90 degrees.

177. The orthopedic implant of claim 174, wherein said surface projections are oriented relative to one another to form an array.

178. The orthopedic implant of claim 174, wherein said surface projections are geometrically disposed relative to one another.

179. The orthopedic implant of claim 174, wherein said exterior surface of said implant is at least in part arcuate.

180. The orthopedic implant of claim 174, wherein at least one of said leading end, trailing end, and sides are curved.

181. The orthopedic implant of claim 174, wherein said sides are curved.

182. The orthopedic implant of claim 174, wherein each of said leading end, trailing end, and sides are curved.

183. The orthopedic implant of claim 182, wherein said leading end, trailing end, and sides form a circle.

184. The orthopedic implant of claim 174, wherein said exterior surface of said implant is at least in part planar.

185. The orthopedic implant of claim 174, wherein said implant is tapered along at least a portion of the length of said implant.

186. The orthopedic implant of claim 174, wherein said implant comprises a material other than bone.

187. The orthopedic implant of claim 174, wherein said implant comprises bone.

188. The orthopedic implant of claim 187, wherein said bone includes cortical bone.

189. The orthopedic implant of claim 174, wherein said implant comprises bone growth promoting material.

190. The orthopedic implant of claim 189, wherein said bone growth promoting material is one of bone morphogenetic protein, hydroxyapatite, and genes coding for the production of bone.

191. The orthopedic implant of claim 174, wherein said implant is treated with a bone growth promoting substance.

192. The orthopedic implant of claim 174, wherein said implant is a source of osteogenesis.

193. The orthopedic implant of claim 174, wherein said implant is at least in part bioabsorbable.

194. The orthopedic implant of claim 174, wherein said implant comprises metal.

195. The orthopedic implant of claim 194, wherein said metal is ASTM material suitable for use as a fusion implant.

196. The orthopedic implant of claim 194, wherein said metal includes titanium.

197. The orthopedic implant of claim 174, wherein said implant comprises a plastic material.

198. The orthopedic implant of claim 174, wherein said implant comprises a ceramic material.

199. The orthopedic implant of claim 174, wherein said implant is formed of a porous material.

200. The orthopedic implant of claim 174, wherein said implant is formed of a material that intrinsically participates in the growth of bone from adjacent bone to adjacent bone through said implant.

201. The orthopedic implant of claim 174, wherein said implant is a motion preserving device adapted to space apart and allow motion between the adjacent bones and bone portions.

202. The orthopedic implant of claim 174, wherein said orthopedic implant is a fusion implant.

203. The orthopedic implant of claim 202, wherein said exterior surface includes at least one opening to permit bone growth from adjacent bone to adjacent bone through said implant.

204. The orthopedic implant of claim 202, wherein said implant has an internal chamber and an access opening for accessing said internal chamber.

205. The orthopedic implant of claim 204, wherein said implant has a cap for closing said access opening.

206. The orthopedic implant of claim 204, wherein said exterior surface includes at least one opening in communication with said internal chamber to permit bone growth from adjacent bone to adjacent bone through said implant.

207. The orthopedic implant of claim 204, wherein said internal chamber is capable of containing bone growth promoting material.

208. The orthopedic implant of claim 207, wherein said bone growth promoting material is one of bone morphogenetic protein, hydroxyapatite, and genes coding for the production of bone.

209. The orthopedic implant of claim 174, further comprising at least one opening capable of retaining fusion promoting materials.

210. The orthopedic implant of claim 174, in combination with a fusion promoting substance.

211. The orthopedic implant of claim 210, wherein said fusion promoting substance includes at least one of bone, bone morphogenetic protein, hydroxyapatite, and genes coding for the production of bone.

212. The orthopedic implant of claim 174, wherein the bases of said first and second surface projections are adjacent to one another.

213. The orthopedic implant of claim 174, wherein the bases of said first and second surface projections are spaced apart from one another along a direction generally parallel to the mid-longitudinal axis of said implant.

214. The orthopedic implant of claim 174, wherein the bases of said first and second surface projections are spaced apart from one another along a direction generally transverse to the mid-longitudinal axis of said implant.

215. The orthopedic implant of claim 174, wherein said forward facets of each of said first and second surface projections face the same direction.

216. The orthopedic implant of claim 174, wherein said opposed side facets intersect each other.

217. The orthopedic implant of claim 216, wherein said opposed side facets converge to form a peak at the top of said surface projection.

218. The orthopedic implant of claim 217, wherein said peaks of at least two of said surface projections are aligned along lines that are at least one of perpendicular, parallel, and diagonal to the mid-longitudinal axis of said implant.

219. The orthopedic implant of claim 217, wherein said peak of said first surface projection overlies at least a portion of said second surface projection.

220. The orthopedic implant of claim 217, wherein said peaks of said first and second surface projections are at the same height above one of said exterior surface of said implant.

221. The orthopedic implant of claim 174, wherein adjacent side facets of adjacent surface projections are spaced apart to define a groove therebetween.

222. The orthopedic implant of claim 174, wherein a plurality of adjacent surface projections are spaced apart to form a plurality of grooves therebetween.

223. The orthopedic implant of claim 222, wherein at least one of said grooves is parallel to the mid-longitudinal axis of said implant.

224. The orthopedic implant of claim 222, wherein at least two of said grooves cross each other.

225. The orthopedic implant of claim 222, wherein at least one of said grooves has a horizontal cross-sectional shape that is one of a v-shape, u-shape, and a box-like shape.

226. The orthopedic implant of claim 174, wherein said side facets have a maximum width therebetween at the bases of said first and second surface projections, the bases being spaced apart from one another by a distance no greater than one-half the maximum width of one of said first and second surface projections.

* * * * *